United States Patent
Petersen

(10) Patent No.: US 6,974,448 B2
(45) Date of Patent: *Dec. 13, 2005

(54) METHOD FOR CONVECTION ENHANCED DELIVERY CATHETER TO TREAT BRAIN AND OTHER TUMORS

(75) Inventor: Daryle Lee Petersen, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 193 days.

This patent is subject to a terminal disclaimer.

(21) Appl. No.: 09/945,471

(22) Filed: Aug. 30, 2001

(65) Prior Publication Data

US 2003/0045866 A1 Mar. 6, 2003

(51) Int. Cl.[7] .................. A61M 25/16; A61M 25/18; A61M 5/00
(52) U.S. Cl. .................. 604/537; 604/534; 604/246
(58) Field of Search .................. 604/890.1, 891.1, 604/19, 27, 28, 500, 508, 94.01, 131, 151–153, 264, 523, 529, 534, 537, 284, 93.01, 164.01, 164.08, 164.09, 164.13, 167.01–167.04, 256

(56) References Cited

U.S. PATENT DOCUMENTS

| | | | |
|---|---|---|---|
| 3,384,089 A | | 5/1968 | Shriner |
| 3,601,320 A | | 8/1971 | Du Plessis |
| 5,425,723 A | | 6/1995 | Wang |
| 5,713,923 A | * | 2/1998 | Ward et al. .................. 607/3 |
| 5,720,720 A | | 2/1998 | Laske et al. |
| 5,978,702 A | * | 11/1999 | Ward et al. .................. 607/3 |
| 6,030,358 A | * | 2/2000 | Odland .................. 604/27 |
| 6,056,725 A | | 5/2000 | Elsberry |
| 6,093,180 A | | 7/2000 | Elsberry |
| 6,350,253 B1 | * | 2/2002 | Deniega et al. .................. 604/164.02 |
| 6,626,885 B2 | * | 9/2003 | Massengale .................. 604/508 |

FOREIGN PATENT DOCUMENTS

| | | | |
|---|---|---|---|
| GB | 1567122 | * | 3/1978 |
| GB | 1567122 | | 5/1980 |

OTHER PUBLICATIONS

Medtronic, Inc., SynchroMed Infusion System, "Optimizing Therapy Through Programmability," 1995 (4 pages).

* cited by examiner

Primary Examiner—Nicholas D. Lucchesi
Assistant Examiner—Catherine S. Williams
(74) Attorney, Agent, or Firm—Banner & Witcoff, Ltd.

(57) ABSTRACT

A method is provided for delivering a therapeutic agent to selected sites within an organism. More particularly, the invention allows for the simultaneous delivery of therapeutics to multiple treatment locations from a single catheter using a single pumping source. The catheter utilizes a microporous membrane that allows for the distribution of therapeutic agents from multiple longitudinal positions.

31 Claims, 3 Drawing Sheets

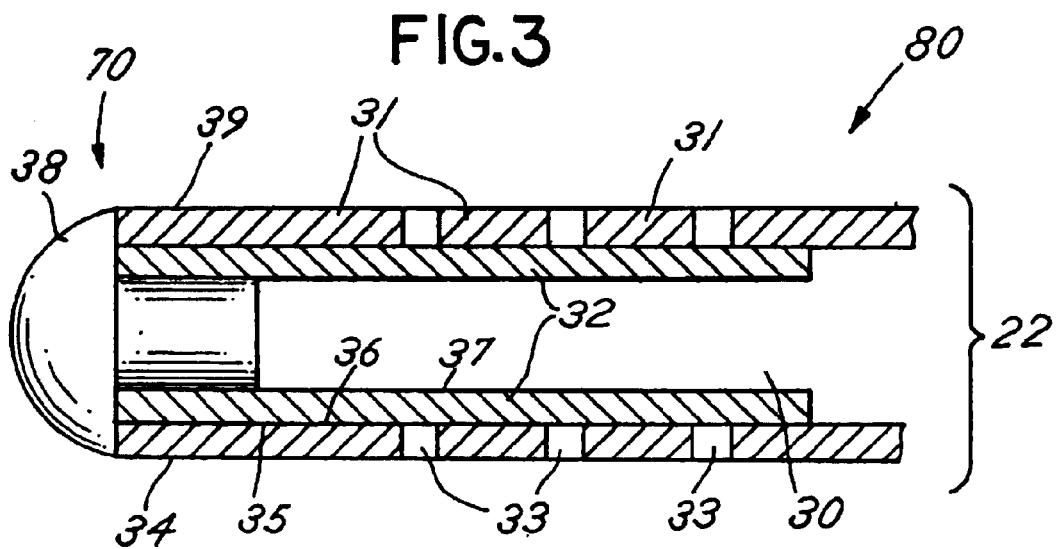
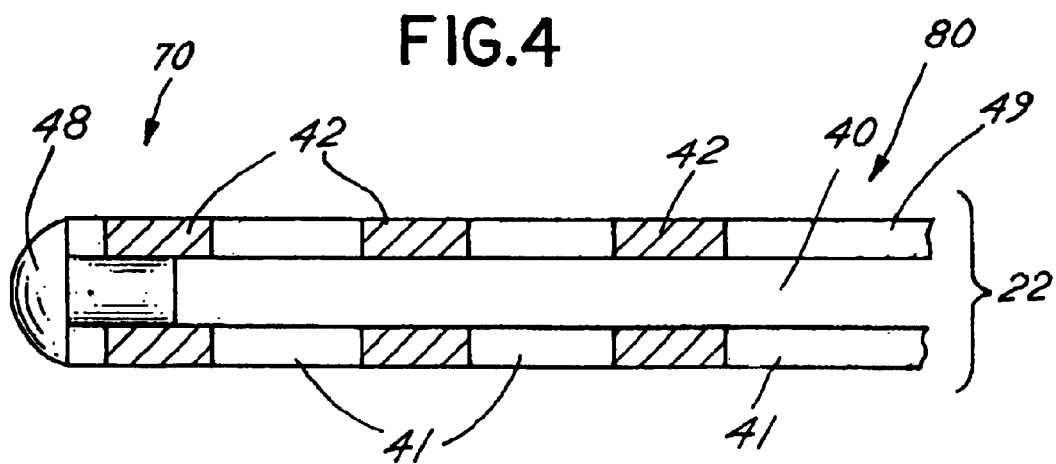

METHOD FOR CONVECTION ENHANCED DELIVERY CATHETER TO TREAT BRAIN AND OTHER TUMORS

FIELD OF THE INVENTION

The present invention relates generally to improvements in catheter design to administer therapeutic agents to organisms. More particularly, this invention allows for the distribution of therapeutic agents from one or more catheters to selected areas using a single pumping device.

BACKGROUND OF THE INVENTION

Catheters have been used for many years to deliver therapeutic agents to patients. In many instances, catheters are implanted in patients that have been diagnosed with diseases that require long-term therapeutic treatment. Diseases that may require catheter implantation include Alzheimer's, Huntington's, epilepsy, neuro-degenerative disorders, and brain tumors. When treating these types of diseases a need arises to deliver therapeutic drugs to multiple locations simultaneously. For example, the difficulty with treating brain tumors is effectively delivering the therapeutic agent to the tumor and the surrounding tissue that is not located near or in the tumor bed. In the case of a patient with a primary brain tumor such as glioblastoma, the tumor and surrounding tissue that may have been infiltrated by cancer cells should be treated. If these outlying tissues are not treated, the tumor may return. Current technology would require the use of multiple separate catheters and pumps to ensure the equal delivery of therapeutics to the tumor and the outlying tissues. The reduction in the number of catheters and the use of a single pump would make a significant improvement over the current treatment practice.

Additionally, in some cases it is optimal to deliver a therapeutic agent through multiple holes rather than through a single hole. Delivery in this manner would promote diffusion of a therapeutic. U.S. Pat. No. 5,720,720 describes convention-enhanced delivery into a brain and other tissue structures using a catheter with a plurality of slit opening symmetrically spaced around the circumference of the catheter. These slit opening function as valves because the slits remain closed until fluid pressure within the catheter forces the slit valves open.

Catheters for simultaneously providing therapeutics to different locations utilizing a single pump have not been available because of the problem of ensuring equal drug diffusion. Presently, multiple hole single catheters are limited to openings that are circumferentially placed along the catheter usually spaced equidistantly apart. Therefore, the only way to achieve fluid distribution at different locations along a longitudinal path is to use multiple pumps and catheters or to use multiple pumps attached to an Image Guided Neurologics Array delivery catheter. The Image Guided Neurologics Array delivery catheter contains multiple catheters each requiring a separate pumping source. Utilizing multiple catheters or pumps increases the risks of surgical complications and adds complexity to the procedure. In addition, it increases cost and patient discomfort.

There exists, therefore, a significant need for a catheter that can distribute therapeutic agents to multiple locations utilizing a single catheter or a single pump. The present invention addresses this need and relates to an improvement in catheters used to administer therapeutic agents to patients.

BRIEF SUMMARY OF THE INVENTION

The present invention recognizes and provides a solution to the problems associated with the distribution of therapeutic agents to multiple locations located along a longitudinal path. The present invention provides a means of distributing therapeutics to selected treatment areas utilizing a single pumping source. Briefly, the invention utilizes a microporous membrane that allows distribution of a therapeutic agent from multiple longitudinal positions on a single catheter, known as diffusion sections, when the internal pressure of the catheter reaches sufficient pressure to overcome the restrictive nature of the microporous membrane, and the internal pressure of the catheter exceeds the external pressure of the surrounding body tissue. When this internal pressure is reached the microporous membrane allows distribution of the therapeutic agent from all the diffusion sections.

Accordingly, an object of the invention is to provide an apparatus that allows for the simultaneous delivery of therapeutics to multiple treatment locations from a single catheter. Current catheters do not allow therapeutics to be delivered from multiple locations along a longitudinal path. In addition, the present invention allows multiple diffusion catheters to be connected to a single pumping source.

Another object of the invention is to provide a less traumatic procedure for patients. The implantation of multiple catheters increases the surgical risks and complexities of the procedure. In addition, increased cost and patient discomfort arise from the use of multiple catheters when the treatment locations are along a generally longitudinal path.

Another object of the invention is the use of a single implantable or external pump with multiple catheters. Use of a single pump reduces patient costs. In addition, a single pump reduces the overall size and weight of the delivery system giving the patient greater mobility.

Yet another object of the invention is that there are no switches or ports in the catheter to malfunction. The diffusion sections do not contain moving parts making the catheter more reliable. Once implanted the catheter can remain in the patient indefinitely, if required.

Yet another object of the invention is that each catheter may be manufactured to meet the needs of each patient. This customization allows for an improved distribution of therapeutic agents in each patient.

The full range of objects, advantages, and features of the invention are only appreciated by a full reading of this specification, and a full understanding of the invention. Therefore, to complete this specification, a detailed description of the invention and the preferred embodiments follow, after a brief description of the drawings wherein additional objects, advantages and features of the invention are disclosed.

BRIEF DESCRIPTION OF THE DRAWINGS

FIG. 3 is a cross sectional view of FIG. 2 illustrating an embodiment of the diffusion section;

FIG. 4 is a cross sectional view of FIG. 2 illustrating a second embodiment of the diffusion section;

DETAILED DESCRIPTION OF THE INVENTION

Figure 1:
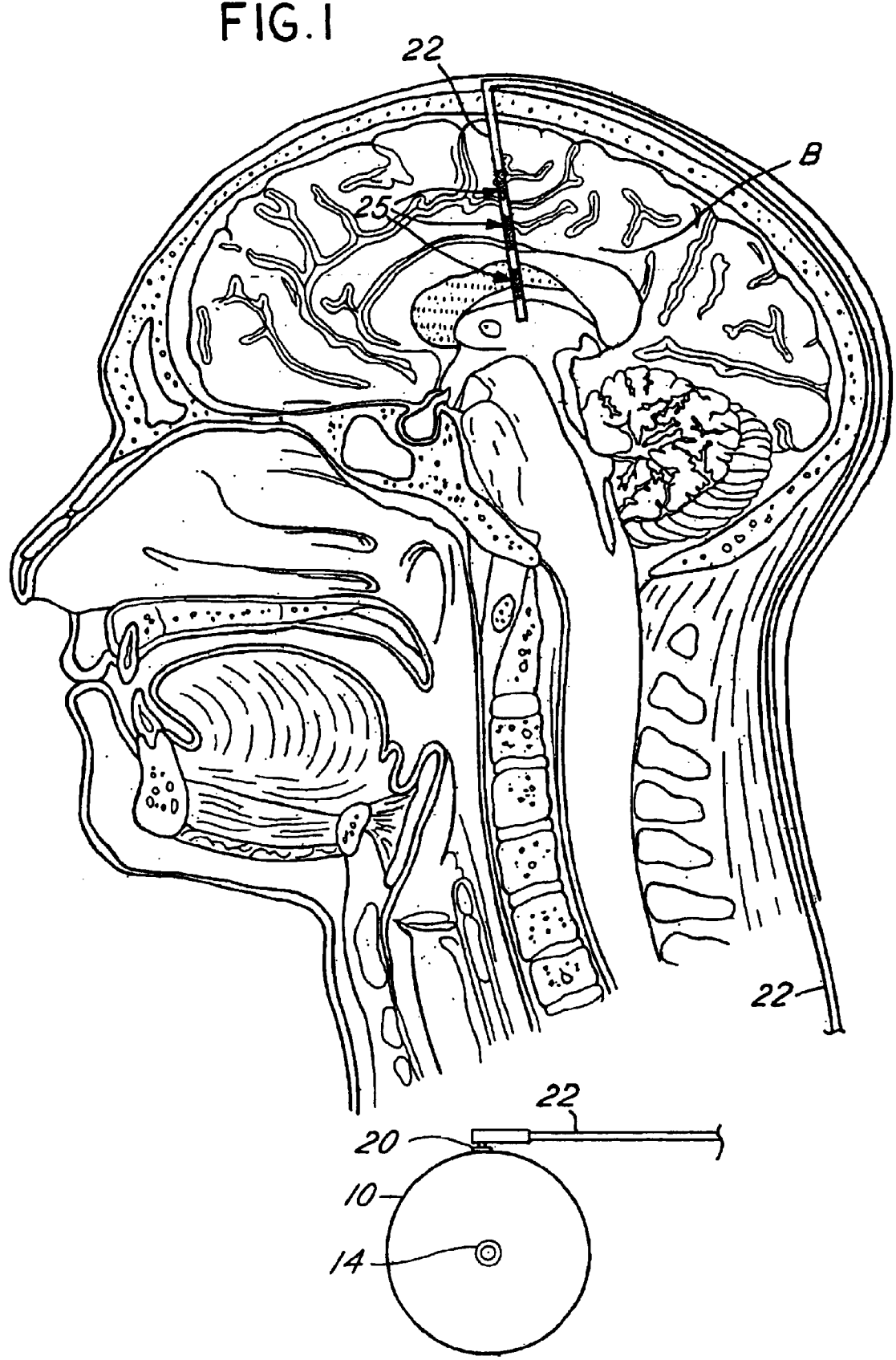
FIG. 1 is a diagrammatic illustration of a diffusion catheter implanted in a brain according to an embodiment of the present invention.

FIG. 1 depicts an embodiment of a catheter system of the present invention in one possible medical application, an intracerebral placement. The system distributes a therapeutic agent to sites the physician selects for treatment. The system uses a pump 10 that can be an external pump or implantable pump like the Medtronic SynchroMed® pump as described in Medtronic brochure "SynchroMed® Infusion System" (1995). As depicted in the figure, the pump 10 has a port 14 into which a hypodermic needle can be inserted to inject a therapeutic to fill the pump 10. As an alternative, the pump 10 may contain a reservoir having a predetermined volume of therapeutic that is pumped at a predetermined rate or according to a programmed rate. The program would initiate the infusion of the therapeutic and would halt therapeutic delivery once the target volume has been reached. In the system shown in FIG. 1, the therapeutic is delivered from the pump 10 though a catheter port 20 into a catheter 22 with diffusion sections 25. The therapeutic is delivered to the physician selected sites through the diffusion sections 25 in the catheter 22. The catheter 22 may be implanted below the skin of a patient using well known stereotactic placement techniques and positioned to deliver the therapeutic to the physician selected sites within the brain B.

With the present invention, the physician predetermines a selected site or sites within the brain and has a catheter made with the diffusion section or sections 25 located at these identified sites. One technique known in the art for predetermining the selected sites would be to have an MRI taken of the effected area. This imaging technique would assist the physician in determining the proper treatment sites. Those skilled in the art will understand that a CT scan, a fluoroscope, or a brain biopsy could also be used to determine the selected sites.

Once the physician selects the sites to be treated with the therapeutic agent and obtains the catheter with the corresponding diffusion sections, the physician implants the catheter 22 with the corresponding diffusion section or sections 25 located at the selected sites. These sites are the preferred drug infusion sites. The catheter 22 is then coupled to the pump 10 through the catheter port 20. The pump 10 is then activated and the catheter system delivers therapeutic agents to the selected sites within the patient. Those in the art will understand that the system utilizing a diffusion catheter could be used to treat other areas of the human body including the heart, liver, or kidney. In addition, the diffusion catheter may have applications in animals.

Figure 2:
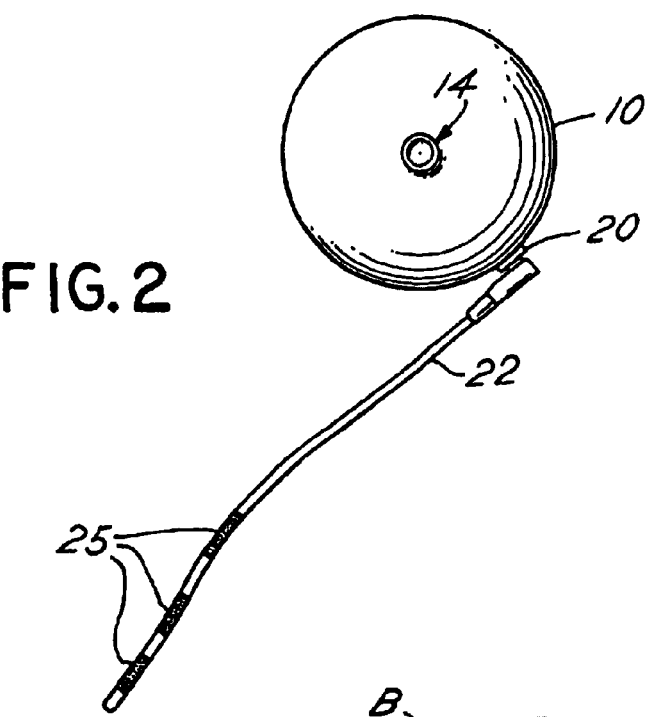
FIG. 2 is a diagrammatic illustration of the improved catheter connected to an implantable infusion pump.

FIG. 2 shows a top view of the pump 10 and the catheter 22 of this invention. The catheter 22 is designed such that a therapeutic can be delivered from multiple positions along the catheter 22. As illustrated in this embodiment, the catheter 22 contains multiple diffusion sections 25 that restrict fluid flow out of the catheter. The pump 10 will fill the catheter with therapeutic until the internal pressure of the catheter 22 reaches sufficient pressure to overcome the restrictive nature of the diffusion sections 25, and the internal pressure of the catheter exceeds the external pressure of the surrounding body tissue. When this internal pressure of the catheter 22 is reached, the therapeutic will disperse though each of the diffusion sections 25. This distribution of therapeutics enables the placement of multiple longitudinally aligned diffusion sections 25 in a catheter 22 for therapeutic delivery to the selected sites.

With the present invention, the treating physician can identify selected sites to receive therapeutics and then select a catheter with the corresponding number of diffusion sections at appropriate longitudinal positions to correspond to the selected sites. For example, a physician may determine that a patient diagnosed with a primary brain tumor should receive therapeutic to both the tumor and to two specific areas outside the tumor bed. In this scenario, a single catheter with three diffusion sections would be utilized alleviating the need for three separate catheters.

FIG. 3 shows an embodiment of the diffusion section. This invention allows the dimensions and shape of the catheter 22 to be varied depending upon the location chosen for administration of the therapeutic agent. The catheter 22 consists of an elongated tubular section 39 having a proximal end 80 and a distal end 70. The tubular section 39 is preferably cylindrical but other configurations may also be used. The tubular section 39 of the catheter 22 has an inner tubular wall 35 and an outer tubular wall 34. In addition, the tubular section 39 has solid section 31 and at least one opening 33 that extends through from the outer tubular wall 34 to the inner tubular wall 35. The openings 33 define diffusion areas. The openings 33 are generally circular shaped holes located around the circumference of the tubular section 39 at various longitudinal positions. The openings 33 allow the therapeutic agent to exit out the catheter 22. Those skilled in the art will understand that the openings 33 can have various shapes provided the openings 33 extends from the inner tubular wall 35 to the outer tubular wall 34. Additionally, the openings 33 can be grouped onto one side of the catheter or may be spaced asymmetrically around the circumference of the tubular section 39. The number of diffusion sections along the longitudinal length of the tubular section 39 is dependant on the number of selected treatment sites.

The solid section 31 of the tubular section 39 is preferably made out of silicon rubber or polyurethane. Those skilled in the art will understand that other flexible, durable biocompatible materials can be used. Further, a radio-opaque material can be added to the solid section 31 to allow for easier viewing of the catheter 22 with imaging. This imaging assists in the placing of the openings 33 at the precise location as determined by the physician.

The catheter 22 of FIG. 3 further includes a microporous membrane 32 that lines the inner wall 35 of the tubular section 39. In one embodiment, the microporous membrane 32 is tubular in shape to fit within the generally circular tubular section 39. The microporous membrane 32 may be composed of a microporous material that is biocompatible and drug compatible such as polysulfone hollow fiber. Alternatively, the microporous membrane 22 may be polyethylene, polyamides, polypropylene, an expanded polytetrafluorethylene (pPTFE), cintered materials, plastics, metals and the like. The microporous membrane 32 consists of an inner wall 37 and an outer wall 36. The inner wall defines a lumen 30 of the catheter 22. The outer wall 36 of the microporous membrane 32 is secured to the inner wall 35 of the tubular section 39. Preferably, the microporous membrane 32 is secured to the inner wall 35 of the catheter 22 through the use of an interference fit between the inner wall 35 of the catheter 22 and the outer wall 36 of the microporous membrane 32. The interference fit is sufficient to hold the membrane in place and prevent therapeutics from bypassing the microporous membrane by traveling between the inner wall 35 of the catheter 22 and the outer wall 36 of the microporous membrane 32, prior to exiting the catheter. Those skilled in the art will understand that as an alternative the microporous membrane could be bonded to the inner wall 35 using a biocompatible and drug compatible adhesive that does not interfere with delivery of the therapeutic agent. In one embodiment, the microporous membrane 32 is preferably secured or attached along the entire length of the elongated tubular section 39. However, those skilled in the art will understand that as an alternative, the microporous membrane 32 can be cut into sections and attached only at the locations of the selected site openings 33 reducing the amount of microporous material needed.

A catheter tip 38 is attached at the distal end 70 of the catheter to prevent the therapeutic from exiting the lumen 30 of the catheter 22 through the distal end 70. The lumen 30 is of sufficient size to allow a therapeutic agent to fill the inner space and to allow the insertion of a stylet to aid in the implantation of the catheter 22. The catheter tip 38 is cylindrical in shape and is designed to fit snugly within the lumen 30 of the tubular section 39 of the catheter 22. In addition, the catheter preferred tip 38 has a curved outer edge. Those in the art will understand that the catheter tip 38 can have alternative shapes to allow for easier insertion at the selected sites. Further the catheter tip 38 may be secured into the catheter 22 using an adhesive that is biocompatible with the catheter tip 38 and the lumen 30 of the tubular section 39 of catheter 22.

During use, the diffusion catheter lumen 30 is filled with the therapeutic agent. The lumen 30 is sized to allow the therapeutic agent to fill the inner space until the internal pressure of the catheter reaches sufficient pressure to overcome the restrictive nature of the microporous membrane, and the internal pressure of the catheter exceeds the external pressure of the surrounding body tissue. When this pressure is reached, the therapeutic agent is dispersed through each of the opening 33.

Turning to FIG. 4, an alternative embodiment of the diffusion catheter 22 is depicted. This embodiment also allows the dimensions and shape of the catheter 22 to be varied depending upon the location chosen for administration of the therapeutic agent. The catheter 22 consists of an elongated tubular section 49 having a proximal end 80 and a distal end 70. The tubular section 49 is preferably cylindrical but other configurations may also be used. The tubular section 49 of the catheter 22 consists of solid sections 41 and microporous membrane sections 42 that form a continuous cross section. The preferred cross section is circular but those in the art will understand that other shapes can be used. The solid sections 41 of the tubular section 49 are preferably made out of a silicon rubber or polyurethane. Those skilled in the art will understand that other flexible, durable biocompatible materials can be used. Further, a radio-opaque material may be added to the solid sections 41 to allow for easier viewing of the catheter with imaging. This imaging assists in placing the microporous membrane sections 42 at the precise location as determined by the physician.

The microporous membrane sections 42 can be made out of a microporous material that is biocompatible and drug compatible such as polysulfone hollow fiber. Alternatively, the microporous membrane sections 42 may be polyethylene, polyamides, polypropylene, expanded polytetrafluorethylene (pPTFE), cintered materials, plastics, metals and the like. The number of microporous sections 42 in the tubular section 49 is dependant on the number of selected treatment sites.

A catheter tip 48 is attached at the distal end 70 of the catheter 22 to prevent the therapeutic from exiting the lumen 40 of the catheter 22 through the distal end 70. The lumen 40 is of sufficient size to allow a therapeutic agent to fill the inner space and to allow the insertion of a stylet to aid in the implantation of catheter 22. The catheter tip 48, of the alternative embodiment is cylindrical in shape and is secured onto the distal end of catheter 22 using an adhesive that is biocompatible with the catheter tip 48 and the lumen 40. In addition, the catheter tip 48 has a curved outer edge. Those in the art will understand that the preferred catheter tip 48 can have alternative shapes to allow for easier insertion at the selected sites. Further, the catheter tip 48 may be designed to fit snugly within the lumen 40 of the tubular section 49 of the catheter 22.

During use, the diffusion catheter lumen 40 is filled with the therapeutic agent. The lumen 40 is sized to allow the therapeutic agent to fill the inner space until the internal pressure of the catheter reaches sufficient pressure to overcome the restrictive nature of the microporous membrane sections, and the internal pressure of the catheter exceeds the external pressure of the surrounding body tissue. When this pressure is reached, the therapeutic agent is dispersed through each of the diffusion sections.

Figure 5:
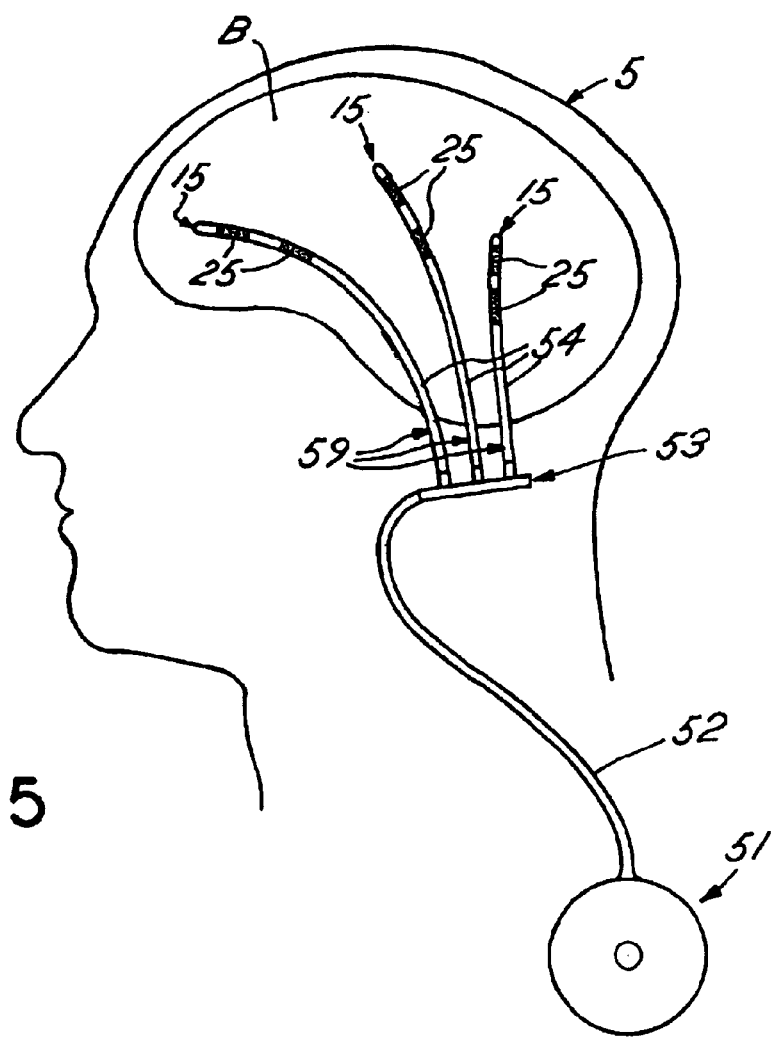
FIG. 5 is a diagrammatic illustration of multiple diffusion catheters implanted in a brain connected to a single pumping source.

FIG. 5 illustrates using multiple diffusion catheters' connected to a single pump 51 in one possible medical application, an intracerebral placement. The system uses a pump 51 that can be an external or an implantable pump like the Medtronic SynchroMed® pump as described in Medtronic brochure entitled "SynchroMed® Infusion System" (1995). The use of a single pump 51 to distribute therapeutic agents to multiple catheters' is possible due to the use of each catheter's diffusion sections. The diffusion sections of each catheter 54 permits the dispersion of therapeutic agent from each catheter diffusion sections. When the internal pressure of the catheters reaches sufficient pressure to overcome the restrictive nature of the diffusion sections, and the internal pressure of the catheters exceeds the external pressure of the surrounding body tissue, the microporous membranes will allow the dispersion of the therapeutic agent. The number of diffusion catheters utilized and the placement of the diffusion sections in each catheter depends upon the treatment plan determined by the physician.

In the system shown in FIG. 5, the therapeutic agent is delivered to selected sites through diffusion sections 25 in catheters 54. The catheters 54 may be implanted below the skin of a patient using well known stereotactic placement techniques and positioned to deliver the therapeutic to physician selected sites within the brain B. The physician will predetermine selected site or sites within the brain and have the catheters made with the diffusion section or sections 25 located at these sites. One technique known in the art for predetermining the selected sites would be to have an MRI taken of the effected area. This imaging technique would assist the physician in determining the proper treatment sites. Those skilled in the art will understand that a CT scan, a fluoroscope, or a brain biopsy could also be used to determine the selected sites.

Once the physician selects the sites to be treated with the therapeutic agent, the physician implants the distal ends 15 of each catheter 54 with the corresponding diffusion section or sections 25 located at the selected drug infusion sites. The proximal ends 59 of each of the diffusion catheters 54 are connected to a common manifold 53 having an entrance and exit openings. The manifold is a device that can be used to connect all the distal catheters and split the flow from the common proximal catheter. The number of utilized diffusion catheters determines the number of exit openings in the manifold. A delivery catheter 52 is connected to the manifold and delivers the therapeutic from the pump 51. The pump 51 is selected to meet the requirements of the diffusion sections in the multiple catheters.

The therapeutic agent is delivered from the pump 51 though the delivery catheter 52 through the manifold 53 to each of the diffusion catheters 54. When the pump 51 is activated the therapeutic is supplied to each of the diffusion catheters 54. When the internal pressure of each of catheters reaches a sufficient pressure to overcome the restrictive nature of the diffusion sections, and the internal pressure of the catheter exceeds the external pressure of the surrounding body tissue, then the therapeutic is distributed from all the diffusion sections at the selected sites within the patient.

An example of this embodiment will illustrate the system. A Parkinson's disease patient with bilateral disease is treated by local drug delivery to specific sites in the basal ganglia. Appropriate delivery sites are chosen and two diffusion catheters are implanted. The mircroporous diffusion catheters are tunneled under the skin and connected to a single pumping source, such as the SynchroMed® pump. The pump is then programmed to deliver the therapeutic agent to the sites. The microporous membrane ensures that dispersion of the therapeutic is delivered from each catheter's diffusion sections.

The description of the apparatus of this invention is not intended to be limiting but is merely illustrative of the preferred embodiment of this invention. Those of ordinary skill in the art will recognize that modifications can be made to a catheter containing a diffusion section described herein without departure from the true spirit and scope of the invention.

The true spirit and scope of the inventions of this specification are best defined by the appended claims, to be interpreted in light of the foregoing specification. Other apparatus which incorporate modifications or changes to that which has been described herein are equally included within the scope of the following claims and equivalents thereof. Therefore, to particularly point out and distinctly claim the subject matter regarded as the invention, the following claims conclude this specification.

I claim:

1. A method of delivering a therapeutic agent to selected sites within an organism, comprising the steps of:
    identifying the selected sites for delivering the therapeutic agent;
    selecting a catheter having a tubular section and a solid catheter tip, the tubular section having a proximal end and a distal end, the distal end attached to the solid catheter tip, the tubular section comprising solid sections and microporous membrane sections, each of the microporous membrane sections including, a first end and a second end, the first end and the second end coupled to the solid sections forming a continuous cross section of the tubular section, the tubular section having a substantially uniform diameter;
    placing the catheter in the organism so that the microporous membrane sections are placed at the selected sites;
    coupling the catheter to a pump for delivering the therapeutic agent to the selected sites;
    actuating the pump to deliver the therapeutic agent to the selected sites through the microporous membrane sections; and
    wherein the catheter is configured to allow the therapeutic agent to fill a lumen of the catheter until a predetermined luminal pressure exceeding the external pressure of the selected site is reached, and the microporous membrane sections are configured to deliver the therapeutic agent at the predetermined luminal pressure.

2. The method as recited in claim 1, wherein the solid section comprises a radio opaque material.

3. The method of claim 1, wherein the pump is an implantable pump.

4. The method of claim 1, wherein the pump is an external pump.

5. A method of delivering a therapeutic agent to selected sites within an organism, comprising the steps of:
    identifying the selected sites for delivering the therapeutic agent;
    selecting at least two catheters, the at least two catheters each comprising a tubular section and a solid catheter tip, the tubular section having a solid section and a microporous membrane section, the microporous membrane section including, a first end and a second end, the first end and the second end coupled to the solid section forming a continuous cross section of the tubular section, the tubular section having a substantially uniform diameter;
    placing the catheters in the organism so that the microporous membrane sections are located at the selected sites;
    connecting each catheter proximal end to a manifold,
    coupling the manifold to a pump for delivering the therapeutic agent to the selected sites;
    actuating the pump to deliver the therapeutic agent to the selected sites; and
    wherein the at least two catheters are configured to allow the therapeutic agent to fill a lumen of the at least tow catheters until a predetermined luminal pressure exceeding the external pressure of the selected site is reached, and the microporous membrane sections are configured to deliver the therapeutic agent at the predetermined luminal pressure.

6. The method as recited in claim 5, wherein the solid section comprises a radio opaque material.

7. The method of claim 5, wherein the pump is an implantable pump.

8. The method of claim 5, wherein the pump is an external pump.

9. A method of delivering a therapeutic agent to selected sites within an organism, comprising the steps of:
    identifying the selected sites for delivering the therapeutic agent;
    selecting at least two catheters, the at least two catheters comprising a tubular section, the tubular section having a solid section and a diffusion area, and an outer tubular wall and an inner tubular wall, the outer tubular wall having at least one opening through to the inner tubular wall, the inner tubular wall lined with a microporous membrane;
    placing each catheter in the organism so that the diffusion area is located at the selected sites;
    connecting each catheter proximal end to a manifold,
    coupling the manifold to a pump for delivering the therapeutic agent to the selected sites;
    actuating the pump to deliver the therapeutic agent to the selected sites; and
    wherein the at least two catheters are configured to allow the therapeutic agent to fill a lumen of the at least two catheters until a predetermined luminal pressure exceeding the external pressure of the selected site is reached, and the diffusion areas configured to deliver the therapeutic agent at the predetermined luminal pressure.

10. The method as recited in claim 9, wherein the catheter solid tubular section comprises a radio opaque material.

11. The method as recited in claim 9, wherein the catheter microporous membrane is located in the diffusion area.

12. The method as recited in claim 9, wherein the catheter microporous membrane further comprises, an outer area and an inner area, the outer area having an interference fit with the inner tubular wall.

13. The method as recited in claim 11, wherein the catheter microporous membrane further comprises, an outer area and an inner area, the outer area having an interference fit with the inner tubular wall.

14. The method of claim 9, wherein the pump is an implantable pump.

15. The method of claim 9, wherein the pump is an external pump.

16. A method of delivering a therapeutic agent to selected sites within an organism, comprising the steps of:
   identifying the selected sites for delivering the therapeutic agent;
   selecting at least two catheters, the at least two catheters each having a proximal end and a distal end, the at least two catheters each having a tubular section, the tubular section including a solid section and at least two diffusion sections, the at least two diffusion sections longitudinally aligned from the distal end corresponding to the selected sites;
   placing each catheter in the organism so that the at least two diffusion sections are located at the selected sites;
   connecting each catheter proximal end to a manifold,
   coupling the manifold to a pump for delivering the therapeutic agent to the selected sites; and
   actuating the pump to deliver the therapeutic agent to the selected site;
   wherein the tubular section further comprises, an outer tubular well and an inner tubular wall, the outer tubular wall having at least one opening within each of the at least two diffusion sections through to the inner tubular wall, the inner tubular wall lined with a microporous membrane; and
   wherein the at least two catheters are configured to allow the therapeutic agent to fill a lumen of the at least two catheters until a predetermined luminal pressure exceeding the external pressure of the selected site is reached, and the diffusions sections confirmed to deliver the therapeutic agent at the predetermined luminal pressure.

17. The method of claim 16, wherein the pump is an implantable pump.

18. The method of claim 16, wherein the pump is an external pump.

19. The method as recited in claim 16, wherein the solid section comprises a radio opaque material.

20. A method of delivering a therapeutic agent to selected sites within an organism, comprising the steps of:
   identifying the selected sites for delivering the therapeutic agent;
   selecting at least two catheters, the at least two catheters each having a proximal end and a distal end, the at least two catheters each having a tubular section, the tubular section including a solid section and at least two diffusion sections, the at least two diffusion sections longitudinally aligned from the distal end corresponding to the selected sites;
   placing each catheter in the organism so that the at least two diffusion sections are located at the selected sites;
   connecting each catheter proximal end to a manifold,
   coupling the manifold to a pump for delivering the therapeutic agent to the selected sites;
   actuating the pump to deliver the therapeutic agent to the selected site;
   wherein the catheter tubular section further comprises, an outer tubular wall and an inner tubular wall, the outer tubular wall having at least one opening within each of the at least two diffusion sections through to the inner tubular wall, the inner tubular wall lined with a microporous membrane, the microporous membrane located at the at least two diffusion sections; and
   wherein the at least two catheters are configured to allow the therapeutic agent to fill a lumen of the at least tow catheters until a predetermined luminal pressure exceeding the external pressure of the selected site is reached, and the diffusions sections configured to deliver the therapeutic agent at the predetermined luminal pressure.

21. The method of claim 20, wherein the pump is an implantable pump.

22. The method of claim 20, wherein the pump is an external pump.

23. The method as recited in claim 20, wherein the solid section comprises a radio opaque material.

24. A method of delivering a therapeutic agent to selected sites within an organism, comprising the steps of:
   identifying the selected sites for delivering the therapeutic agent;
   selecting at least two catheters, the at least two catheters each having a proximal end and a distal end, the at least two catheters each having a tubular section, the tubular section including a solid section and at least two diffusion sections, the at least two diffusion sections longitudinally aligned from she distal end corresponding to the selected sites;
   placing each catheter in the organism so that the at least two diffusion sections are located at the selected sites;
   connecting each catheter proximal end to a manifold,
   coupling the manifold to a pump for delivering the therapeutic agent to the selected sites;
   actuating the pump to deliver the therapeutic agent to the selected site;
   wherein the catheter tubular section further comprises, an outer tubular wall and an inner tubular wall, the outer tubular wall having at least one opening within each of the at least two diffusion sections through to the inner tubular wall, the inner tubular wall lined with a microporous membrane, the microporous membrane further comprising, an outer area and an inner area, the outer area having an interference fit with the inner tubular wall; and
   wherein the at least tow catheters are configured to allow the therapeutic agent to fill a lumen of the at least tow catheters until a predetermined luminal pressure exceeding the external pressure of the selected site is reached, and the diffusions sections configured to deliver the therapeutic agent at the predetermined luminal pressure.

25. The method of claim 24, wherein the pump is an implantable pump.

26. The method of claim 24, wherein the pump is an external pump.

27. The method as recited in claim 24, wherein the solid section comprises a radio opaque material.

28. A method of delivering a therapeutic agent to selected sites within an organism, comprising the stops of:
   identifying the selected sites for delivering the therapeutic agent;

selecting at least two catheters, the at least two catheters each having a proximal end and a distal end, the at least two catheters each having a tubular section, the tubular section including a solid section and at least two diffusion sections, the at least two diffusion sections longitudinally aligned from the distal end corresponding to the selected sites;

placing each catheter in the organism so that the at least two diffusion sections are located at the selected sites;

connecting each catheter proximal end to a manifold, coupling the manifold to a pump for delivering the therapeutic agent to the selected sites;

actuating the pump to deliver the therapeutic agent to the selected site;

wherein the catheter tubular section further comprises, an outer tubular wall and an inner tubular wall, the outer tubular wall having at least one opening within each of the at least two diffusion sections through to the inner tubular wall, the inner tubular wall lined with a microporous membrane, the microporous membrane located at the at least two diffusion sections, the microporous membrane further comprising, an outer area and an inner area, the outer area having an interference fit with the inner tubular wall; and wherein the at least two catheters are configured to allow the therapeutic agent to fill a lumen of the at least two catheters until a predetermined luminal pressure exceeding the external pressure of the selected site is reached, and the diffusions sections configured to deliver the therapeutic agent at the predetermined luminal pressure.

29. The method of claim 28, wherein the pump is an implantable pump.

30. The method of claim 28, wherein the pump is an external pump.

31. The method as recited in claim 28, wherein the solid section comprises a radio opaque material.

* * * * *